United States Patent [19]

Ratcliffe et al.

[11] Patent Number: 5,942,434
[45] Date of Patent: Aug. 24, 1999

[54] NUCLEIC ACID CONSTRUCTS COMPRISING HYPOXIA RESPONSE ELEMENTS

[75] Inventors: Peter John Ratcliffe, Kidlington; John David Firth, Oxford; Adrian Llewllyn Harris, Oxford; Christopher William Pugh, Oxford; Ian James Stratford, Derbyshire, all of United Kingdom

[73] Assignee: Oxford Biomedica (UK) Limited, Oxford, United Kingdom

[21] Appl. No.: 08/693,174

[22] PCT Filed: Feb. 15, 1995

[86] PCT No.: PCT/GB95/00322

§ 371 Date: Dec. 12, 1996

§ 102(e) Date: Dec. 12, 1996

[87] PCT Pub. No.: WO95/21927

PCT Pub. Date: Aug. 17, 1995

[30] Foreign Application Priority Data

Feb. 15, 1994 [GB] United Kingdom .................. 9402857

[51] Int. Cl.[6] ............................ C12N 15/00; C12N 15/63; C07H 21/04; A01N 43/04
[52] U.S. Cl. ..................... 435/320.1; 435/455; 435/69.1; 435/69.8; 435/69.3; 435/325; 424/93.21; 514/44; 536/23.5
[58] Field of Search .......................... 514/44; 435/172.3, 435/69.1, 69.8, 69.3, 320.1, 325, 455; 424/93.21; 536/23.5

[56] References Cited

U.S. PATENT DOCUMENTS

| | | | |
|---|---|---|---|
| 5,332,671 | 7/1994 | Ferrara et al. | 435/240.1 |
| 5,399,346 | 3/1995 | Anderson et al. | 424/93.21 |

FOREIGN PATENT DOCUMENTS

| | | |
|---|---|---|
| 0 333 201 | 9/1989 | European Pat. Off. . |
| 93/25234 | 12/1993 | WIPO . |
| 95/12678 | 5/1995 | WIPO . |
| 95/13376 | 5/1995 | WIPO . |

OTHER PUBLICATIONS

K. Blanchard et al. "Hypoxic Induction of the Human Erythropoietin Gene: Cooperation Between the Promoter and Enhancer, Each of Which Contains Steroid Receptor Response Elements", Molecular and Cellular Biology, vol. 12, No. 12, pp. 5373–5385, Dec. 1992.

C. Bauer, "Erythropoietin– From Gene Structure to Therapeutic Applications", J. Perinat. Med. vol. 23, p. 77–81, 1995.

S. Imagawa et al., "Regulatory elements of the erythropoietin gene", Blood, vol. 77, pp. 278–285, Jan. 15, 1991.

P. Maxwell et al., "Inducible operation of the erythropoietin 3' enhancer in multiple cell lines: Evidence for a widespread oxygen–sensing mechanism", Proc. Natl. Acad. Sci., vol. 90, pp. 2423–2427, Mar. 1993.

R. Vile et al., "In Vitro and in vivo targeting of gene expression to melanoma cells", Cancer Research, vol. 53, pp. 962–967, Mar. 1, 1993.

B. Lim et al., "Retrovirus–mediated gene transfer of human adenosine deaminase: Expression of functional enzyme in murine hematopoietic stem cells in vivo", Mol. Cell. Biol., vol. 7, No. 10, pp. 3459–3465, Oct. 1987.

G. Semenza et al., "Hypoxia–inducible nuclear factors bind to an enhancer element located 3' to the human erythropoietin gene", Proc. Natl. Acad. Sci., vol. 88, pp. 5680–5684, Jul. 1991.

C. Pugh et al., "Functional analysis of an oxygen–regulated transcriptional enhancer lying 3' to the mouse erythropoietin gene", Proc. Natl. Acad. Sci., vol. 88, pp. 10553–10557, Dec. 1991.

Eck & Wilson, 'Gene–Based Therapy.' In: Goodman's & Gilman's The Pharmacological Basis of Therapeutics, Ninth Edition, McGraw–Hill Health Professions Division, Chapter 5, pp. 77–101, 1995.

Dachs et al., Nature Medicine, vol. 3, No. 5, pp. 515–520, May 1997.

Orkin et al., Report and Recommendations of the Panel to Assess the NIH Investment in Research on Gene Therapy, Dec. 7, 1995.

Hanania, American Journal of Medicine, vol. 99, No. 5, p. 537–552, Nov. 1995.

Mullen et al., Proceedings of the National Academy of Sciences of the USA, vol. 89, No. 1, pp. 33–37, Jan. 1, 1992.

*Primary Examiner*—Deborah Crouch
*Assistant Examiner*—Jill D. Martin
*Attorney, Agent, or Firm*—Wenderoth, Lind & Ponack, L.L.P.

[57] ABSTRACT

Nucleic acid constructs comprising hypoxia response elements in operable linkage with a coding sequence of a gene of interest are disclosed. In particular, such nucleic acid constructs comprise genes encoding pro-drug activation systems or cytokines.

22 Claims, 6 Drawing Sheets

HepG2

MEL

Fig. 2A

```
GAATTCTACC ...140bp.. TGGCCCCTTC GCGCCACCTT CTACTCCTCC
EcoRI                      Δ
Δ D0                       D4

CCTAGTCAGG AAGTTCCCCC CCGCCCCGCA GCTCGCGTCG TGCAGGACGT
                           Δ          Δ          Δ
                           D8         D9         D10

GACAAATGGA AGTAGCACGT CTCACTAGT
    Δ                    SpeI
    D11
```

NUCLEIC ACID CONSTRUCTS COMPRISING HYPOXIA RESPONSE ELEMENTS

BACKGROUND OF THE INVENTION

1. Field of the Invention

This invention is concerned with hypoxically-inducible expression control sequences, nucleic acid constructs comprising such sequences, and their use for selective targeting of anti-cancer therapy and other kinds of therapy where target cells are affected by hypoxia.

2. Detailed Description of the Related Art

Vile and Hart (1993) describe a method in which certain gene promoters, which are preferentially active in melanocytic cells, were used to direct gene expression of a reporter gene specifically to melanoma cells in vitro, and in vivo in mice. Constructs consisting of the promoters and the beta-galactosidase gene were directly injected into mice and the reporter gene was expressed in melanoma cells and in some normal melanocytes but not in surrounding normal tissue. However, tissue-specific promoters will necessarily be limited in the tumours that they can target and will also be liable to target normal cells of the tissue concerned (as was noted in Vile and Hart above).

SUMMARY OF THE INVENTION

Cancers tend to outgrow the blood supply and often have areas of hypoxia and necrosis which distinguish them from normal tissue. This feature also makes tumours resistant to radiation due to low oxygen levels and x-ray treatment becomes less effective. Certain genes such as the gene for erythropoietin, are known to be regulated by hypoxia. Erythropoietin is a hormone which regulates erythropoiesis and hence blood oxygen content. Cis-activating DNA sequences that function as tissue-specific hypoxia-inducible enhancers of human erythropoietin expression have been identified (Semenza et al, 1991). A DNA enhancer sequence located 3' to the mouse erythropoietin gene has been shown to confer oxygen-regulated expression on a variety of heterologous promoters (Pugh et al, 1991). It has further been demonstrated that the oxygen-sensing system which controls erythropoietin expression is widespread in mammalian cells (Maxwell et al, 1993).

A second example of a hypoxia-associated regulator is a regulator which lies 5' to the mouse phosphoglycerate kinase gene promoter. The sequence of the regulator has been published (McBurney et al, 1991) but its hypoxia inducible properties have not previously been considered or defined in the literature. It has now been recognised by the inventors that the native sequence of the regulator has hypoxically-inducible features. The nucleotides responsible have been defined and the inventors have shown that repeating the sequence leads to increased induction of the gene whose expression is controlled. Further, the inventors have shown that using the interleukin-2 gene under tissue-specific promoters is an effective strategy for specific targeting of tumours.

There are anti-cancer drugs that become activated under hypoxia (Workman and Stratford, 1993), but the use of a drug activation system where the enzyme activating the drugs is greatly increased under hypoxia will provide a far superior therapeutic effect.

The invention provides a nucleic acid construct comprising at least one gene encoding a species having activity against disease, operatively linked to a hypoxically inducible expression control sequence.

When the construct is present in a suitable host cell, expression of the gene will thus be regulated according to the level of oxygenation. Preferably the expression control sequence is a promoter or enhancer. In a host cell under hypoxic conditions, expression of the gene will be initiated or upregulated, while under conditions of normoxia (normal oxygen level) the gene will be expressed at a lower level or not expressed at all. The expression level may vary according to the degree of hypoxia. Thus, a gene product which has therapeutic activity can be targeted to cells affected by disease, eg. tumour cells.

The species encoded by the gene in the construct according to the invention may be for example a cytokine, such as interleukin-2 (IL-2) which is known to be active in the immune response against tumours. Genes encoding other molecules which have an anti-tumour effect may also be used.

In a preferred embodiment of the construct according to the invention, the species encoded by the gene is a pro-drug activation system, for example the thymidine phosphorylase enzyme, which converts a relatively inactive drug into a much more potent one. Transfection of the thymidine phosphorylase gene into human breast cancer cells has been shown to greatly increase the sensitivity of the cancer cells to 5-deoxy-5FU (see Example 8). The thymidine phosphorylase gene has not previously been reported as an agent for gene therapy. Another pro-drug activation system which can be used is cytosine deaminase, which activates the pro-drug 5-fluorocytosine (5-FC) to form the antitumour agent 5-fluorouracil (5-FU). A further example of a pro-drug activation system for use in the invention is cytochrome p450 to activate the drug SR4233 (Walton et al, 1992).

The construct according to the invention may contain more than one gene and more than one type of gene. Additional genes may encode further species having activity against disease, or they may have gene products with other activities.

DESCRIPTION OF THE DRAWINGS

FIGS. 1A–1B.

FIGS. 2A–2B.

FIGS. 8A–8C. In FIGS. 8A–8C, the CD2 induction data was measured with oxygen at 5%, 2%, 1%, 0.001% ($N_2$, almost no oxygen), 0% $O_2$ ($AnO_2$). n represents the number of experiments performed. CD2 expression was measured immediately following treatment (Oh) and five hours post-treatment (5 h).

FIGS. 9A–9B.

Hypoxically-inducible promoters or enhancers may be chosen from those referred to herein, or they may be other hypoxically-inducible promoters or enhancers. It is anticipated that other hypoxically-inducible promoters or enhancers will be discovered; oxygen-sensing systems are widespread in mammalian cells and many genes are likely to be under hypoxic control.

Preferably, the nucleic acid construct according to the invention comprises at least one hypoxia response element which confers hypoxia inducibility on the expression control sequence. There may be for example two or more hypoxia response elements linked so as to increase hypoxia inducibility and thus to increase the induction of the gene or genes under hypoxia. Hypoxia response elements may be chosen from among those referred to herein, or they may be other hypoxia response elements. As noted above, oxygen-sensing systems are widespread in mammalian cells, and it is expected that other hypoxia response elements will be found.

The following hypoxia response elements may be used in the construct according to the invention:
a). The following portion of the transcriptional enhancer lying 3' to the mouse erythropoietin (Epo) gene:

GGG CCC TAC GTG CTG CCT CGC ATG G (25) [SEQ ID NO: 1]

b) One of the following portions of the 5' flanking sequence of the mouse phosphoglycerate kinase (PGK) gene:

CGC GTC GTG CAG GAC GTG ACA AAT (P24) [SEQ ID NO: 2] or

GTC GTG CAG GAC GTG ACA (P18) [SEQ ID NO: 3]

These PGK sequences have not been previously recognised as having hypoxically-inducible properties.

All of these sequences have counterparts in human genes and are highly conserved between species. They are also well characterised.

The invention therefore also provides a hypoxically inducible expression control sequence which comprises the nucleic acid sequence:

CGC GTC GTG CAG GAC GTG ACA AAT (P24) [SEQ ID NO: 2] or

GTC GTG CAG GAC GTG ACA (P18) [SEQ ID NO: 3]

or a nucleic acid sequence with substantial homology thereto. These sequences can be found in EMBL database, accession no. M18735, at nucleotides 631 to 654 and 634 to 651.

The construct according to the invention may comprise more than one eg. three or more copies of one of the Epo or PGK sequences given above. Additionally or alternatively, a longer portion of the Epo or PGK-1 enhancer or flanking sequence may be used in the construct, which longer portion comprises the hypoxia response element and part of the surrounding sequence.

Hypoxically-inducible expression control sequences and hypoxia response elements may be chosen so as to be operative in particular tissues or cell types to be targeted therapeutically, or they may be chosen to work in a wide range of tissues or cell types.

The invention further provides a nucleic acid construct as described herein for use in the treatment of a patient suffering from a disease in which hypoxia is a cause or a symptom or is otherwise present. Alternatively, the invention provides a method of treatment of a patient suffering from a disease in which hypoxia is a cause or a symptom or is otherwise present, which method comprises administering to the patient a nucleic acid construct as described herein.

The nucleic acid constructs will be useful for treating cancer patients. In hypoxic tumour cells, the physiological stimuli will be such that the gene which has activity against the disease is expressed. Although it may be very difficult to get all cells to take up the gene to switch it on, experiments show that even with 10% of cells expressing the thymidine phosphorylase gene there is an effect on other cells which results in a 10-fold increase in sensitivity of the whole population. This is known as the bystander effect and is probably due to active metabolites of the anticancer drug passing from one cell to another. Since this drug kills proliferating cells, it should still have much less toxicity on normal tissue than on cancer cells. Sometimes, nearby normal cells will also express the gene and the active drug or cytokine or other species encoded by the gene will be able to diffuse from the normal cells into the tumour.

The inventors have demonstrated both stable and transient transfection of cells with genes under the control of hypoxically inducible enhancers. Transient transfection only lasts for a few days, whereas stably transfected genes insert into the cell genome and can persist indefinitely. Stable transfection may prove to be necessary for therapeutic applications of the invention but it is possible that transient transfection will be sufficient.

Administration of constructs according to the invention for therapeutic purposes can be by injection of DNA directly into the solid tumour. Certain types of cell including tumour cells, skin cells and muscle cells take up naked DNA, and tumour cells do so particularly well. The constructs may thus be administered in the form of naked DNA plasmids. Alternatively other vectors such as retroviruses may be used.

A suitable therapeutic regime will be direct injection of DNA into the affected site, and administration of pro-drug in the case of a construct encoding a pro-drug activation system, optionally combined with radiotherapy.

Although the invention is described above in relation to targeting of tumour cells, it will also be useful in other types of disease where hypoxia occurs, including for example coronary artery disease and strokes. The nucleic acid construct may comprise a gene encoding a pro-drug activation system for a suitable drug or the gene may encode a cytokine or a growth factor. A vascular growth factor can be used to stimulate new blood vessel formation in hypoxic areas and expression of the growth factor by the construct will then be automatically switched off when the area becomes revascularised.

The inventors have carried out deletional analysis and mutational analysis of the mouse Epo enhancer sequence, in the cell lines HepG2 and a23 (a23 are non-Epo producing cells). Transient tranfection experiments were performed using plasmids containing full or partial enhancer sequences lying 1.4 kb 5' to the $\alpha_1$ globin reporter gene.

Three critical sites for enhancement were defined, corresponding to the nucleotides 5–12, 21–24 and 33–34 of the 96 nucleotide enhancer sequence (mouse Epo enhancer: EMBL accession no. X73471). All three regions were absolutely necessary for enhancer function in the above experiments. But overall, studies indicated that the 1–25 or 1–26 nucleotide sequence has hypoxically inducible operation (EMBL, X73471, nucleotides 407 to 431 or 432. Inducible operation via the 1–26 nucleotide sequence was also demonstrated for MEL and HeLa cells, which have previously been found unable to support oxygen-regulated reporter gene expression using plasmids containing the 1–96 nucleotide enhancer sequence (Maxwell et al 1993). A total of 19 cell lines (some unreported) have now been tested by the inventors and none has been found to lack the capacity to modulate oxygen dependent changes in reporter gene expression by the sequence 1–26. Thus, whereas it was previously suggested that the hypoxically inducible response was not universal in mammalian cells, it now seems more likely that it is.

Recent studies of the human Epo enhancer also define at least three critical regions of the sequence (Semenza et al 1992 and Blanchard et al 1992).

The examples which follow contain experimental demonstrations by the inventors which indicate the manner in which different aspects of the invention work.

EXAMPLES

Figure 1A:
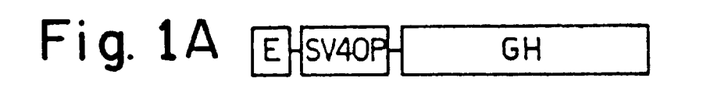
FIG. 1A shows the structure of the test plasmids, where E represents Epo enhancer sequence, SV40P represents the SV40 early promoter and GH represents the body of the growth hormone gene.
Figure 1B:
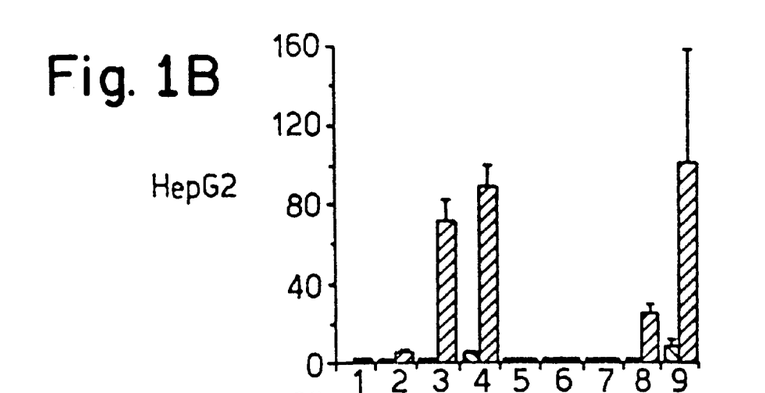
FIG. 1B shows the independent experiments measuring hypoxic inducible activity of the constructs comprising the Epo enhancer sequence.
Figure 1C:
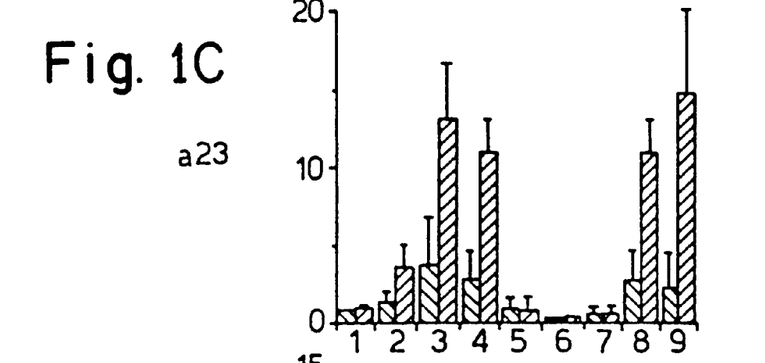
Figure 1D:
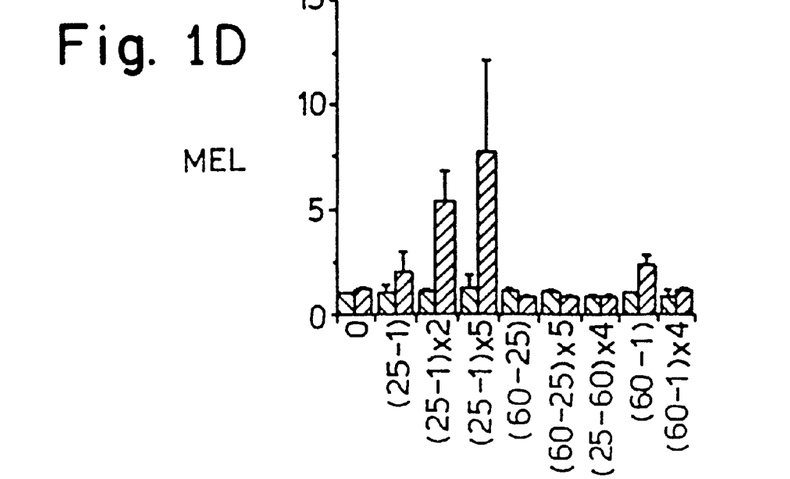

Example 1
Action of Subsequences from the Mouse Epo Enhancer on an Adjacent SV40 Promoter FIG. 1(A) shows the structure of the test plasmids, where E represents Epo enhancer sequence, SV40P represents the SV40 early promoter and GH represents the body of the growth hormone gene. The Epo enhancer sequence (E) used in each test plasmid is indicated beneath the corresponding bars of the histogram. A co-transfected plasmid containing the $\alpha_1$ globin gene alone (pBSα$^-$) was used to correct for transfection efficiency. Expression is normalised to that of the enhancerless pSVGH in normoxic cells and represents the mean ± S.D. of three independent experiments (B). Inducible activity is conveyed by sequence 1–25 in all cell types. Inducible activity was much increased by concatamerization of this sequence which also conveyed some constitutive activity in normoxic cells $(1–25)_2$ and $(1–25)_5$. In contrast, neither constitutive nor inducible activity was conveyed by sequence 25–60 in any cell type. Concatamers of this sequence were tested in either orientation $(25–60)_3$ and $(60–25)_4$ but none had any action. The monomeric sequence 1–60 was more active than the monomeric sequence 1–25 in HepG2 cells and a23 but not MEL cells.

Example 2
Oxygen-Regulated Control Elements in the PGK-1 and LDH-A Genes

The materials and methods below are employed in Examples 3–6.

Cell Lines and Culture Conditions

The cell lines used were HepG2 (human hepatoma), HeLa (human cervical carcinoma) and L cells (mouse fibroblast) grown in minimal essential medium, with Earle's salts, supplemented with fetal bovine serum (10%), glutamine (2 mM), penicillin (50 units/ml) and streptomycin sulfate (50 μg/ml). For assay of endogenous gene expression, and for preparation of nuclear extracts, cells were grown to approximately 70% confluence. The medium was then replaced, and cells subjected to the following conditions for 14–16 hours: (1) normoxia (20% oxygen, with 5% $CO_2$ and 75% $N_2$); (2) hypoxia (1% oxygen, with 5% $CO_2$ and 94% $N_2$ in Napco 7100 incubator); (3) hypoxia with cycloheximide (100 μM); (4) normoxia with cobaltous chloride (50 μM); (5) normoxia with cyanide (100 μM); (6) hypoxia with cyanide (100 μM).

Transient Transfection

In all experiments the test plasmid (10–100 μg), containing either human $\alpha_1$ globin (α) or human growth hormone (GH) as a reporter, was cotransfected with a control plasmid (10–50 μg) using electroporation as previously described (Pugh et al. 1991). The control plasmid, whose expression was not altered by hypoxia, was either the human $\alpha_1$ globin gene, when the test plasmid contained GH; or FGH, a fusion gene consisting of the mouse ferritin promoter (290 bp) linked to the human growth hormone gene, when the test plasmid contained the α globin gene.

Details of test plasmid design are as follows. The mouse PGK-1 5' flanking sequence used in the basic construct (pPGKGH) was a 502 bp fragment of the PGK-1 sequence in pDEneo, extending from the EcoR1 site at −523 bp (1=translational initiation) to the Taql site at −21 bp. The nucleotide sequence of the mouse PGK-1 gene is shown in SEQ ID No. 4, which is the same sequence as found in EMBL database, accession no. M18735 mentioned above. The translation start of the sequence is nucleotide 946. Accordingly, −523 bp to −21 bp correspond to nucleotide 423 to nucleotide 925 of SEQ ID No. 4. The mouse LDH-A gene sequence in pLDHGH was generated by PCR amplification from mouse genomic DNA of a 233 bp fragment (−186 to +47 from transcriptional start site) using oligonucleotides derived from published sequence. The nucleotide sequence of the mouse LDH-A gene is shown in SEQ ID No. 5. The transcription start of the sequence is nucleotide 1118. Accordingly, −186 bp to +47 bp correspond to nucleotide 932 to nucleotide 1164 of SEQ ID No. 5. Plasmid DNA for transfection was purified on a caesium gradient; nucleotide sequence of the crucial elements of all plasmids was confirmed by direct sequencing.

After electroporation transfected cells were spilt equally and incubated in parallel for 14–16 hours in 8 ml of culture medium in 100 mm Petri dishes under normoxic or hypoxic conditions, or exposed to chemical agents, as described above.

RNA Analysis

RNA was extracted, analysed by RNase protection, and quantitated as previously described (Pugh et al 1991). For assay of transiently transfected material 3–10 μg of RNA was subjected to double hybridisation with probes which protected 120 bp of GH mRNA and either 132 bp (α132) or 97 bp (α97) of α globin mRNA, depending on whether the test or control plasmid contained α globin.

For assay of endogenous PGK-1 gene expression 50 μg of RNA extracted from HepG2 cells was hybridised with a riboprobe which consisted of 121 bp from the 5' end of the exon 3 of the human PGK-1 gene, together with 68 bp of adjacent intron (obtained by PCR of genomic DNA and cloning by standard methods). For assay of endogenous LDH-A gene expression 25 μg of RNA obtained from L cells was hybridised with a riboprobe which consisted of 47 bp from the 5' end of exon 1 of the mouse LDH-A gene, together with adjacent 5' flanking sequence (obtained by PCR of genomic DNA and cloning by standard methods). In these experiments a small quantity (0.5 μg) of RNA extracted from K562 cells (a human Epo cell line which expresses α globin mRNA abundantly) was added to each sample before hybridisation, and the samples were probed concurrently with the α97 probe in addition to the PGK-1 or LDH-A probe. This provided a means of determining that sample processing and gel loading was comparable between specimens.

Nuclear Extract

Cells were cooled rapidly, harvested into ice cold phosphate buffered saline, and pelleted at 2000 g. A modification of Dignam's protocol was used to prepare nuclear extract. Briefly, cells were swollen for 10 minutes in Buffer A (10 mM Tris-HCl pH 7.4, 10 mM KCl, 1.5 mM $MgCl_2$), lysed using a Dounce homogenizer, and extracted for 30 minutes in Buffer C (20 mM Tris-HCl, pH 7.4, 420 mM KCl, 1.5 mM $MgCl_2$, 20% glycerol). Nuclear debris was pelleted at 10000 g and the supernatant dialysed for 2 hours against Buffer D (20 mM Tris-HCl pH 7.4, 100 mM KCl, 0.2 mM EDTA, 20% glycerol). The entire procedure was performed at 4° C. using precooled buffers. In addition buffers A and C contained phenylmethysulfonyl fluoride, 0.5 mM; aprotinin, 1 $\mu$g/ml; leupeptin, 1 $\mu$g/ml; pepstatin, 1 $\mu$g/ml; sodium orthovanadate, 1 mM; benzamidine, 0.5 mM; levamisole, 2 mM; $\beta$ glycerophosphate, 10 mM; DTT, 0.5 mM. Sodium orthovanadate and DTT were also added to buffer D. Following dialysis, aliquots of nuclear extract were frozen in a dry ice/ethanol bath and stored at −70° C.

Electrophoretic Mobility Shift Assays

Oligonucleotides used as probes or competitors were purified by polyacrylamide gel electrophoresis. Labelling was performed with {gamma-$^{32}$P}ATP (3000 Ci/mmol) using $T_4$ polynucleotide kinase. Labelled oligonucleotides were annealed with 4×molar excess of the complementary strand. Unlabelled oligonucleotides were annealed in molar equivalent quantities.

The binding reactions were performed in a 20 $\mu$l volume containing 50 mM KCl, 1 mM $MgCl_2$, 0.5 mM EDTA, 5 mM DTT, 5% glycerol, and 0.15–0.30 $\mu$g of sonicated polydldC. Nuclear extract (5 $\mu$g unless otherwise stated) was incubated with this mixture for 5 minutes at room temperature, before probe (approximately 0.5 ng)and specific competitors were added. Incubation was continued for a further 10 minutes. Reactions were electrophoresed (12.5 v/cm) at 4° C. using 5% polyacrylamide in 0.3×TBE (pH 7.3 at 4° C.).

Example 3

RNA Analysis of PGK-1 and LDH-A Gene Expression

Expression of the endogenous human PGK-1 gene in HepG2 cells and of the endogenous mouse LDH-A gene in L cells was assayed by RNA analysis. Cells were exposed for 16 hours to normoxia (20% $O_2$) hypoxia (1% $O_2$) and cycloheximide 100 $\mu$M, normoxia and cobaltous chloride 50 $\mu$M, normoxia and cyanide 100 $\mu$M, hypoxia and cyanide 100 $\mu$M. 50 mg RNA was used for each hybridisation reaction. For each gene, both hypoxia and exposure to cobalt led to a 2–3 fold induction of gene expression. The protein systhesis inhibitor cycloheximide abrogated the response to hypoxia. Cyanide did not affect the hypoxic response, neither inducing expression in normoxia, nor preventing induction by hypoxia.

Example 4

Location of Sequences Responsible for Hypoxia Inducible Expression of the Endogenous PGK-1 and LDH-A Genes Portions of the 5' flanking sequence of PGK-1 and LDH-A genes were linked to a growth hormone receptor gene. Expression in transfected HepG2 cells of fusion genes containing either a 502 bp fragment from the PGK-1 enhancer/promoter region (pPGKGH) or a 233 bp sequence from the LDH-A promoter (pLDHGH), was measured after exposure to conditions of hypoxia, normoxia etc. as used in Example 3. In each case hypoxically inducible expression was conveyed by the sequences, a somewhat greater level of inducibility being observed than for the respective endogenous gene. The inducible operation of these sequences contrasted with the SV40 virus promoter, the a globin promoter, the ferritin promoter and the herpes simplex thymidine kinase promoter, none of which had this property. Responses were not specific for HepG2 cells and similar inducible responses were obtained in transfected HeLa cells.

In this example, 5 $\mu$g of RNA was used for each hybridisation reaction, and the $\alpha$132 and GH probes were used to detect expression of the transfection control and test plasmids respectively.

Example 5

Deletional Analysis of the PGK-1 Enhancer Region

Figure 2A:
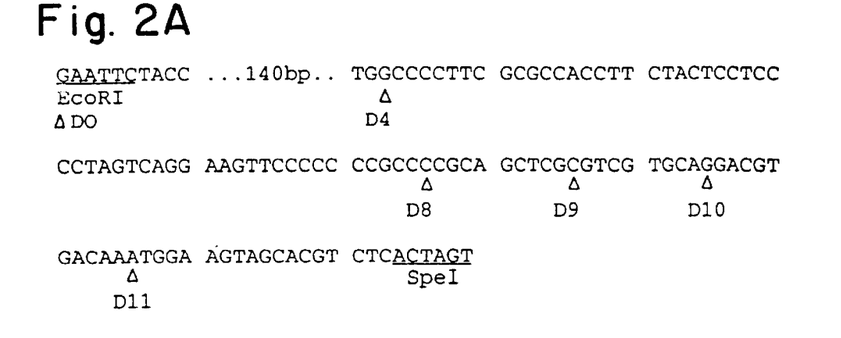
FIG. 2A shows the partial nucleotide sequence of the 253 bp EcoR1-Spe1 fragment containing the enhancers (EMBL accession No. M18735, nucleotides 417 to 676). The position of the deletions (D) from the 5' end of the sequence are marked by arrows.
Figure 2B:
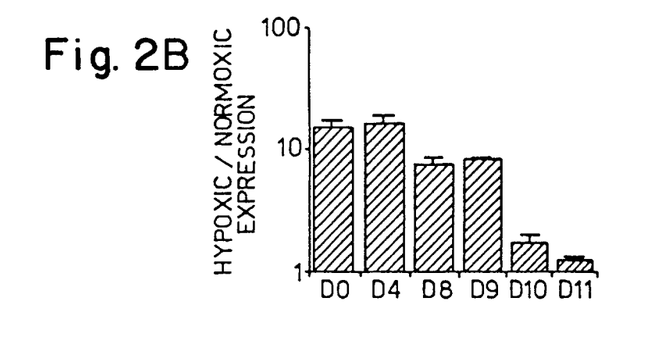
FIG. 2B shows the ratio of hypoxic to normoxic expression conferred on the reporter by EcoR1-Spe1 fragment and deletion thereof. Values represent means of three separate transfections, with bars showing SEM.

FIG. 2 shows (A) partial nucleotide sequence of the 253 bp EcoR1-Spe1 fragment containing the enhancers (EMBL accession no. M18735, nucleotides 417 to 676). The positions of deletions (D) from the 5' end of the sequence are marked by arrows. FIG. 2(B) shows the ratio of hypoxic to normoxic expression conferred on the reporter by EcoR1-Spe1 fragment and deletion thereof. Values represent means of three separate transfections, with bars showing SEM.

A series of nested deletions was carried out as indicated in FIG. 2. The greatest reduction in the amplitude of hypoxic induction occurred with deletion of 20 bp between D9 and D11. The functional importance of this region was confirmed by the finding that a pGKGH fusion gene from which 18 bp between the positions of D9 and D11 had been removed no longer demonstrated hypoxic inducibility.

Example 6

Functional Analysis of the Oxygen Regulated Element of the PGK Enhancer

For analysis of the functional characteristics of this isolated sequence (the 18 bp sequence described in Example 5), oligonucleotides were cloned into a site 10 bp 5' to the TATA box of the herpes simplex thymidine kinase promoter in a thymidine kinase—growth hormone fusion gene. The 18 bp element (P18) whose deletion abrogated hypoxic induction of the PGKGH construct, was capable of conferring responsiveness to hypoxia when placed in either orientation. Concatamers operated more powerfully than monomers. Extension of P18 to a 24 bp element (P24) did not lead to increased activity.

Example 7

Stable Transfection of Cells with the PGK-1 Hypoxic Promoter

HeLa cells were transfected by electroporation with supercoiled plasmid DNA. Stably transfected cells were selected by growth in G418 medium. Two plasmids were transfected. The first contained a hypoxic promoter coupled to the gene for the cell surface marker CD2 and the second contained the same hypoxic promoter coupled to the gene for the enzyme cytosine deaminase as well as a constitutively acting promoter (SV40 early region promoter) coupled to a neomycin resistance region. The hypoxic promoter used in this transfection experiment consisted of a 456 bp Sph-1/Taq-1 fragment from the mouse PGK-1 5' flanking sequence into which 3 copies of the active sequence P24 had been inserted at the Spe-1 site.

This system was designed in order to enable us to create signal pathway mutant cells. Essentially the CD2 and cytosine deaminase genes are being used as selectable markers and the neomycin resistance gene provides a means of retaining the transfected plasmid and therefore selecting cells which have lost the response rather than the transfected genes. It is clear that the principle of selectable markers can be used to kill unwanted cells, according to the invention.

After transfection cells were grown for two weeks and pools were subject to a 16 hour incubation at either 21% oxygen (normoxia) or 1% oxygen (hypoxia). Marker gene expression was quantified by RNA analysis. Approximately 10 fold increased expression was observed at 1% oxygen versus 21%. Thus, the selectable marker genes were under the control of the hypoxically inducible promoter.

Example 8
Transfection of Human Breast Cancer Cell Line with Thymidine Phosphorylase Gene Human breast cancer cells of the cell line MCF-7 were transfected with a gene for thymidine phosphorylase. Thymidine phosphorylase can convert a relatively inactive drug into a much more potent product. The gene is suitable for linking up with hypoxically-inducible promoters/enhancers.

As a general principle, when genes are transfected into cancer cells they will be expressed at different levels and so it is important to study several different clones of the cells to see the variability.

Results of drug sensitivity experiments are shown in FIGS. 3–7. −7, −4, −12, +4 and +16 are all derivatives of MCF-7 which have been transfected with the thymidine phosphorylase gene.

Figure 3:
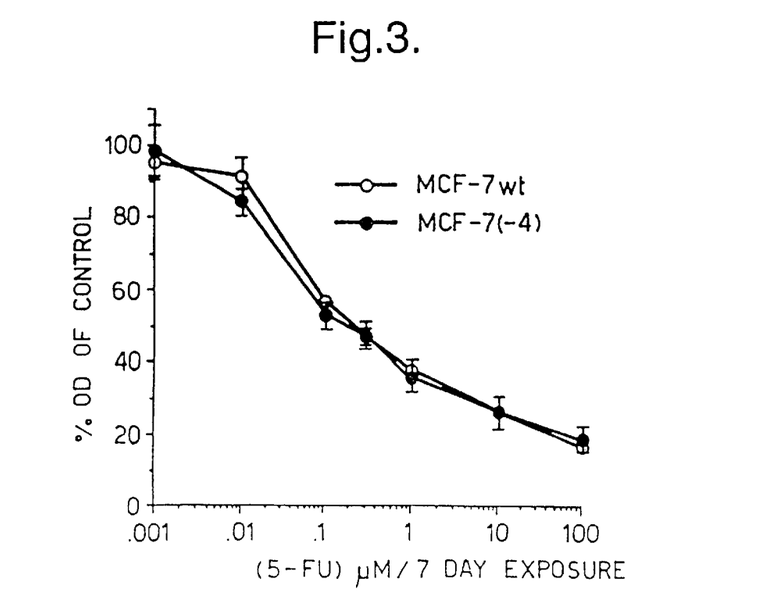
FIG. 3 shows a survival curve for the parent cell line MCF-7 in breast cancer (WT) and a derivative from it that has been transfected with a gene for thymidine phosphorylase, MCF-7(−4).
Figure 4:
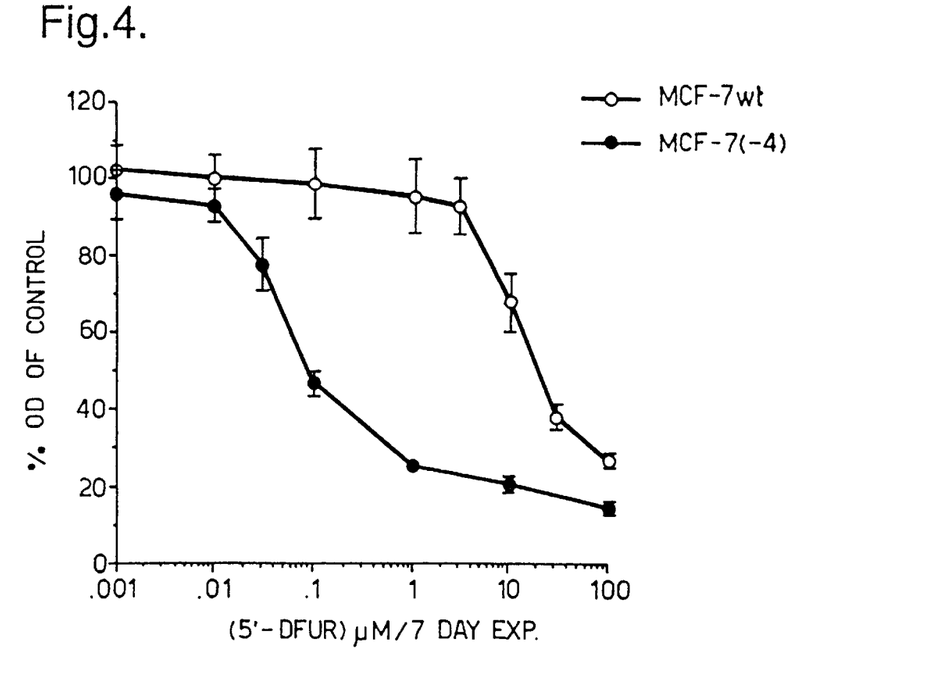
FIG. 4 shows the drug sensitivity results of transfectant (−4) to 5-deoxy 5FUdR as compared to the wild-type.

FIG. 3 shows a survival curve for the parent cell line MCF-7 in breast cancer (WT) and a derivative from it that has been transfected with a gene for thymidine phosphorylase. There is relatively little difference in their sensitivity to the drug 5FU. However, the transfectant (−4) is nearly 200 fold more sensitive to 5-deoxy 5FUdR (FIG. 4).

Figure 5:
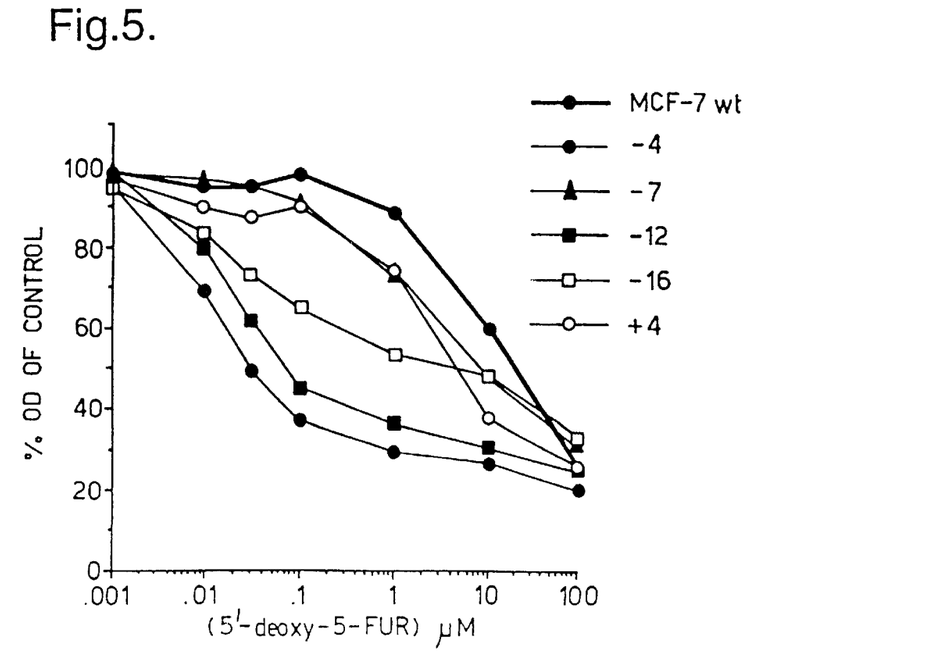
FIG. 5 shows the drug sensitivity results of clones −4, −7, −12, −16, and +4 to 5-deoxy 5FUdR compared to the wild-type.
Figure 6:
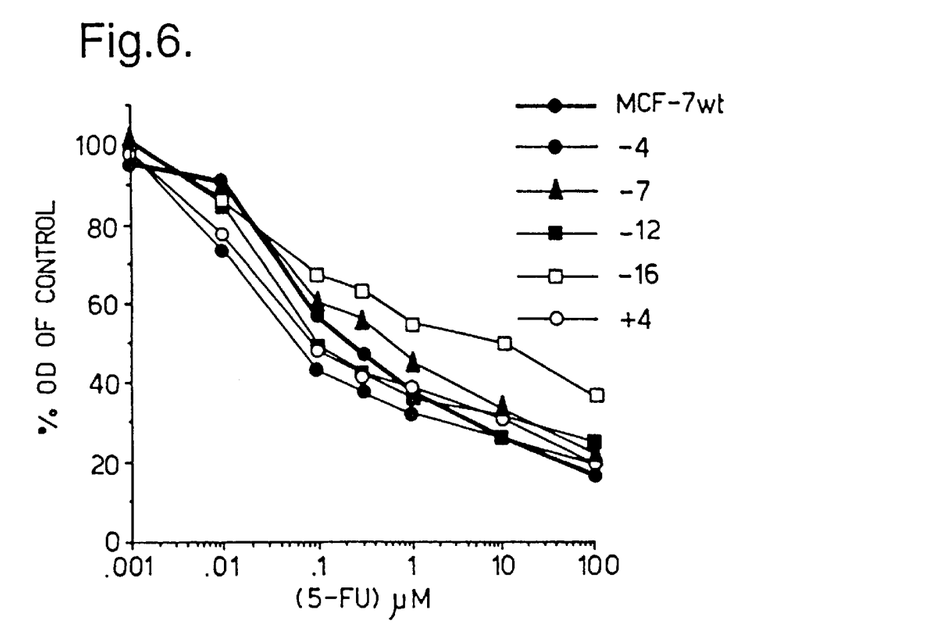
FIG. 6 shows the drug sensitivity results of clones −4, −7, −12, −16, and +4 to 5FU.
Figure 7:
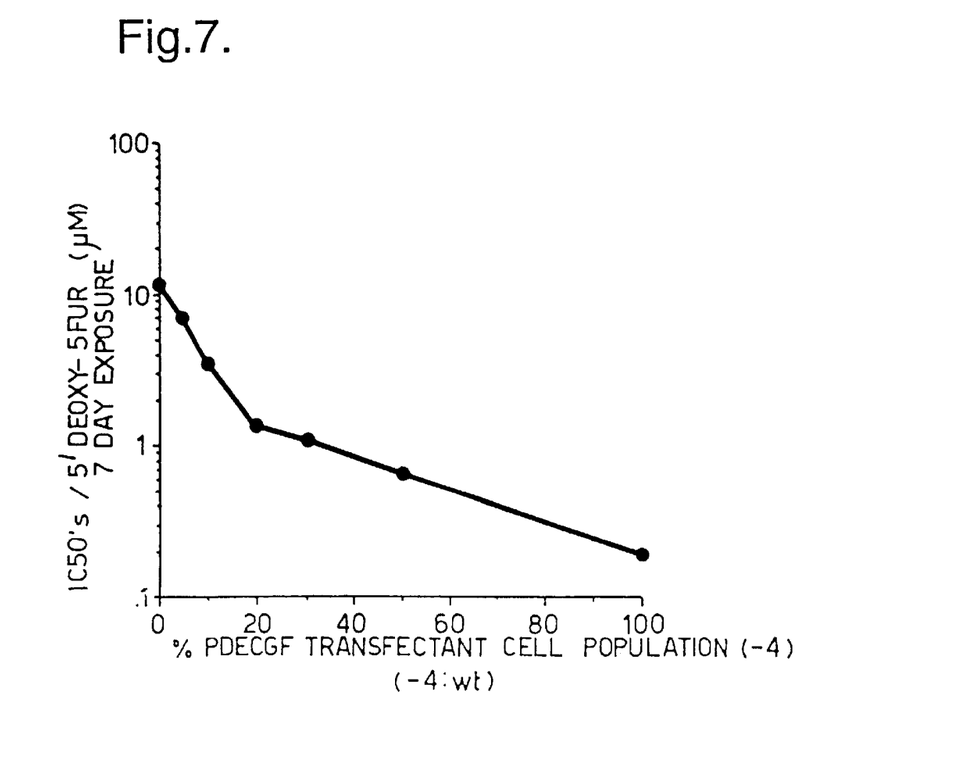
FIG. 7 shows the drug sensitivity results of the mixed cell population (-4:wt) to 5-deoxy 5FUdR.

FIG. 5 shows clones −12 and −4 are particularly sensitive to the drug 5-deoxy 5FUdR compared to the wild-type. Two other transfectants −7 and +4 and −16 are a little bit more sensitive than the wild-type. Note that there is a log scale and therefore the IC50 (the concentration of drug required to inhibit growth by 50%) is more than 100 times lower for the transfectants −12 and −4. Therefore, the expression of one gene at a higher level can make these cells 100 times more sensitive to chemotherapy. Clearly there is variation depending on the level of expression and therefore we want to be able to switch on as high as possible. The pro-drug 5-deoxy 5FUdR is broken down to 5FU and a comparison of the sensitivity of the cells to 5FU in FIG. 6 reveals that there is really very little difference. This means that it is the activation step that is important rather than downstream events.

Finally, when a drug has been activated by the cancer cells it could be transferred to other cells which would normally be resistant but the active form of the drug can overcome this. To demonstrate, the sensitive cells (−4 cells) and the wild-type cells were mixed together, and it can be seen from FIG. 7 that the IC50 drops from 11.6 $\mu$M to 1.5 $\mu$M i.e. one log 10-fold increase in sensitivity with only 20% of the cells expressing the drug activation gene. Thus, in gene therapy it will not be necessary to get all of the cells to express the gene, only perhaps 20%.

This demonstrates that the target gene thymidine phosphorylase is useful as a mechanism of activating an anticancer drug and that overexpressing it in even a proportion of cells can confer drug sensitivity, not only these cells but adjacent cells.

Example 9
Stable Transfection of Cells with PGK-1 Hypoxically Inducible Elements and Different Promoters The PGK-1 hypoxia response element was evaluated within the context of the PGK-1 gene promoter (M3), the 9–27 gene promoter (9-3C) and the thymidine kinase gene promoter (sTK5).

The constructs were similar to those described in Example 7. The promoters and PGK-1 hypoxia response elements were placed upstream of genes encoding the endothelial CD2 surface protein and the negative selectable marker cytosine deaminase. The 9–27 and thymidine kinase promoters were each used with 3 copies of the P18 PGK-1 element and the PGK-1 gene promoter was used with 3 copies of the P24 PGK-1 element.

The stable transfectants were tested for their response to severe hypoxia (0.001% and 0% $O_2$) and different levels of oxygen (0.1, 1, 2, 5 and 20% $O_2$). Cell-surface expression of transfected CD2 was analysed using fluorescence-labelled anti-CD2 antibodies. Labelled cells were assayed for CD2 expression on a fluorescence activated cell sorter.

The increase in CD2 production depended on the length and severity of hypoxia. Following severe hypoxia, CD2 expression in the transfected lines only increased following subsequent aeration (maximal at 5 hours post hypoxia), whereas, following less severe hypoxia conditions, CD2 expression peaked immediately after hypoxia.

1% $O_2$ induced CD2 expression, but not to the same degree as severe hypoxia (<5 ppm). 5% and 20% $O_2$ did not result in any CD2 induction.

CD2 expression persisted for 24 hours following reoxygenation.

Figure 8A:
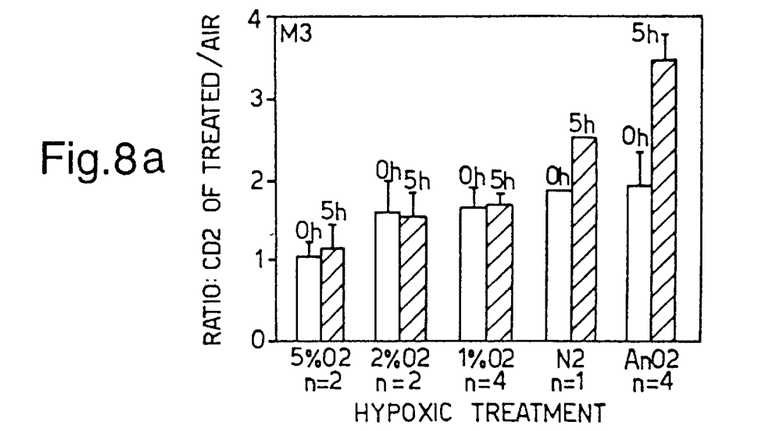
FIG. 8A shows CD2 induction data for M3.
Figure 8B:
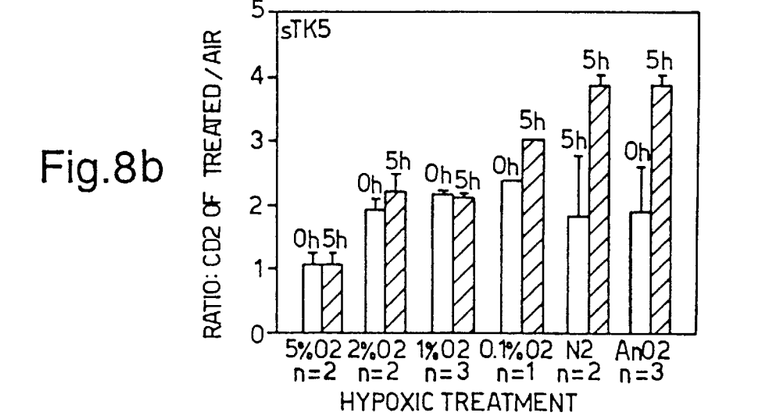
FIG. 8B shows CD2 induction data for sTK5.
Figure 8C:
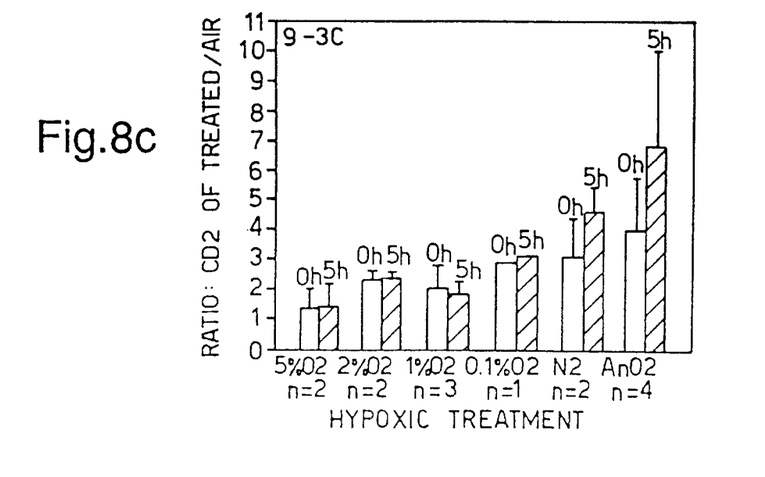
FIG. 8C shows CD2 induction data for 9-3C.

FIGS. 8a, b and c show CD2 induction data for M3, sTK5 and 9-3C respectively, with oxygen at 5%, 2%, 1%, 0.001% ($N_2$, almost no oxygen), 0% $O_2$ (An$O_2$). n represents the number of experiments performed. CD2 expression was measured immediately following treatment (0h) and five hours post-treatment (5 h).

Example 10
Hypoxia-Induced Pro-Drug Sensitisation

The bacterial enzyme cytosine deaminase catalyses the conversion of cytosine to uracil, and can therefore change the pro-drug 5-fluorocytosine (5-FC) to the antitumour agent 5-fluorouracil (5-FU).

Transfected cells (9-3C and M3) as described in Example 9 were tested for sensitivity to 5-FC. Cells were subjected to hypoxic exposure (16 hours), followed by exposure to 5-FC or 5-FU (24 hours), followed by a 96 hour growth delay.

Figure 9A:
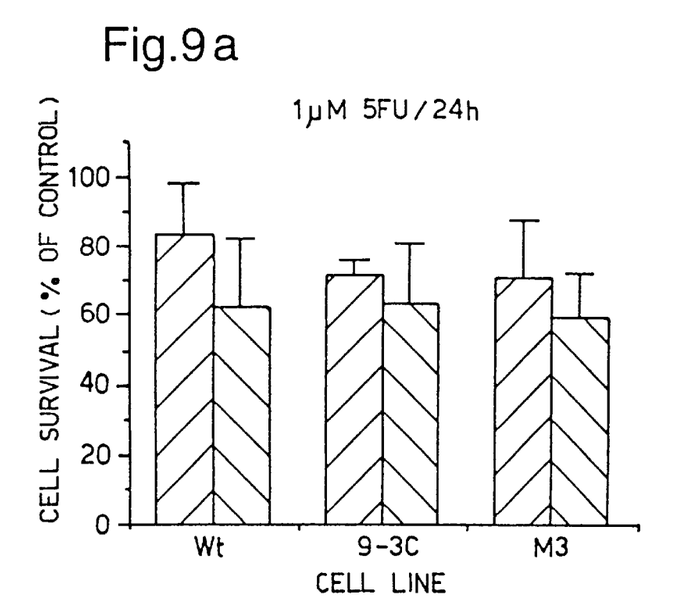
FIG. 9A shows drug sensitivity results of transfected cells 9-3C and M3 to 5-FU post-hypoxia.
Figure 9B:
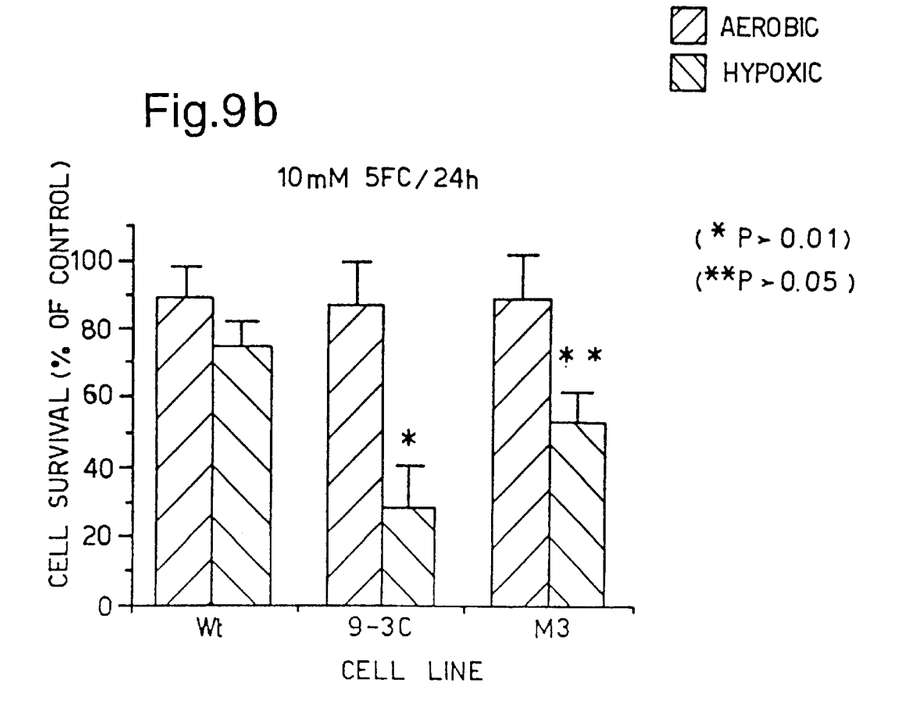
FIG. 9B shows drug sensitivity results of transfected cells 9-3C and M3 to 5-FC post-hypoxia.

Results are shown in FIGS. 9a and b (Wt represents non-transfected HT1080 cells). M3 and 9-3C cell lines were significantly more sensitive to 5-FC post-hypoxia (FIG. 9a). There was no significant difference in 5-FU sensitivity in control (Wt) or transfectant cells following hypoxic or normoxic treatment (FIG. 9b).

Example 11
In vivo Experiment in Mice

Tumour cells (HT1080 cells) were transfected with a DNA construct containing the CD2 gene linked to a promoter containing the PGK-1 hypoxia response element (as described in Example 9). About a million transfected cells were implanted under the skin of a mouse. The tumour was later excised and histologically sectioned. Staining with anti-CD2 antibodies indicated hypoxically-induced expression of the marker gene.

REFERENCES

Blanchard, K. L. Acquaviva, A. M. Galson, D. L. and Bunn, H. F. (1992) Mol. Cell. Biol. 12, 5373–5385.
Maxwell P. H., Pugh C. W. and Ratcliffe P. J. (1993), Proc. Natl. Acad. Sci. USA, vol. 90, p.2423–2427.
McBurney M. W., Sutherland L. C, Adra C. N., Leclair B. et al (1991), Nucleic Acids Research, vol 19, no. 20, p. 5755–5761.

Pugh C. W., Tam C. C., Jones R. W. and Ratcliffe P. J. (1991), Proc. Natl. Acad. Sci. USA, vol. 88, p.10553–10557.

Pugh C. W., Ebert B. L., Ebrahim O. and Ratcliffe P. J. (in press), Biochimica et Biophysics Acta.

Semenza G. L., Nejjfelt M. K., Chi S. M. and Antonarakis S. E. (1991), Proc. Natl. Acad. Sci. USA, vol. 88, p.5680–5684.

Semenza, G. L. & Wang, G. L. (1992) Mol. Cell. Biol. 12, 5447–5454.

Vile R. G. and Hart I. R. (1993), Cancer Research, vol 53, p.962–967.

Walton M. I., Wolf C. R., Workman P. (1992), Biochem Pharmacol., vol 44, p. 251–259.

Workman P. and Stratford I. J. (1993), Cancer and Metastasis Reviews, vol 12, p.73–82.

We claim:

1. A nucleic acid construct comprising a hypoxia response element, wherein said hypoxia response element is a phosphoglycerate kinase sequence between about nucleotide −523 to about nucleotide −21 of the mouse PGK-1 gene which is nucleotide 423 to nucleotide 925 of SEQ ID No. 4, or a hypoxia-responsive fragment thereof, operably linked to a coding sequence other than the mouse PGK-1 coding sequence.

2. The nucleic acid construct according to claim 1, wherein the hypoxia-responsive fragment comprises the nucleic acid sequence of SEQ ID No. 2.

3. The nucleic acid construct according to claim 1, wherein the hypoxia-responsive fragment comprises the nucleic acid sequence of SEQ ID No. 3.

4. The nucleic acid construct according to claim 1, which further comprises an additional one or more of said hypoxia response elements.

5. A nucleic acid construct comprising a hypoxia response element, wherein said hypoxia response element is a lactate dehydrogenase sequence between about nucleotide −186 to about nucleotide +47 of the mouse LDH-A gene which is nucleotide 932 to nucleotide 1164 of SEQ ID No. 5, or a hypoxia-responsive fragment thereof, operably linked to a coding sequence other than the mouse LDH-A coding sequence.

6. The nucleic acid construct according to claim 5, which further comprises an additional one or more of said hypoxia response elements.

7. A nucleic acid construct comprising two or more hypoxia response elements, wherein said hypoxia response elements consist of two or more copies of the nucleic acid sequence of SEQ ID NO. 1, operably linked to a coding sequence.

8. A method for preparing a nucleic acid construct according to claim 1, comprising the steps of:

(a) providing a hypoxically inducible expression control sequence between about nucleotide −523 to about nucleotide −21 of the mouse PGK-1 gene which is nucleotide 423 to nucleotide 925 of SEQ ID No. 4, or a hypoxia-responsive fragment thereof;

(b) providing a nucleic acid sequence encoding a gene product, other than mouse PGK-1; and (c) operably linking the hypoxically inducible expression control sequence to the nucleic acid sequence.

9. The method according to claim 8, wherein the hypoxia-responsive fragment comprises the nucleic acid sequence of SEQ ID No. 2.

10. The method according to claim 8, wherein the hypoxia-responsive fragment comprises the nucleic acid sequence of SEQ ID No. 3.

11. The method according to claim 8, wherein the gene product is an enzyme which converts a prodrug to an active drug.

12. The method according to claim 11, wherein the enzyme is cytosine deaminase.

13. The method according to claim 8, wherein the gene product is a cytokine.

14. A method for preparing a nucleic acid construct according to claim 5, comprising the steps of:
   (a) providing a hypoxically inducible expression control sequence between about nucleotide −186 to about nucleotide +47 of the mouse LDH-A gene which is nucleotide 932 to nucleotide 1164 of SEQ ID No. 5, or a hypoxia-responsive fragment thereof;
   (b) providing a nucleic acid sequence encoding a gene product, other than mouse LDH-A; and
   (c) operably linking the hypoxically inducible expression control sequence to the nucleic acid sequence.

15. The method according to claim 14, wherein the gene product is an enzyme which converts a prodrug to an active drug.

16. The method according to claim 15, wherein the enzyme is cytosine deaminase.

17. The method according to claim 15, wherein the gene product is a cytokine.

18. A method for preparing a nucleic acid construct according to claim 7, comprising the steps of:
   (a) providing two or more hypoxically inducible expression control sequences which consist of two or more copies of the nucleic acid sequence of SEQ ID No. 1;
   (b) providing a nucleic acid sequence encoding a gene product; and
   (c) operably linking the hypoxically inducible expression control sequences to the nucleic acid sequence.

19. The method according to claim 18, wherein the gene product is an enzyme which converts a prodrug to an active drug.

20. The method according to claim 19, wherein the enzyme is cytosine deaminase.

21. The method according to claim 18, wherein the gene product is a cytokine.

22. An isolated DNA consisting of SEQ ID No. 2 or 3.

* * * * *

SEQUENCE LISTING

<160> NUMBER OF SEQ ID NOS: 5

<210> SEQ ID NO 1
<211> LENGTH: 25
<212> TYPE: DNA
<213> ORGANISM: Murinae gen. sp.

<400> SEQUENCE: 1

```
gggccctacg tgctgcctcg catgg                                    25
```

<210> SEQ ID NO 2
<211> LENGTH: 24
<212> TYPE: DNA
<213> ORGANISM: Murinae gen. sp.

<400> SEQUENCE: 2

```
cgcgtcgtgc aggacgtgac aaat                                     24
```

<210> SEQ ID NO 3
<211> LENGTH: 18
<212> TYPE: DNA
<213> ORGANISM: Murinae gen. sp.

<400> SEQUENCE: 3

```
gtcgtgcagg acgtgaca                                            18
```

<210> SEQ ID NO 4
<211> LENGTH: 1110
<212> TYPE: DNA
<213> ORGANISM: Murinae gen. sp.

<400> SEQUENCE: 4

```
ggatccacgg cctctggccg cattttacca ctgagctaca ctcccaaagc agtcgaaat     60 acagtggccc aggattgaaa tgatcactta gatgctttgc agtcttgata agacactaaa   120
tctttgtcta tcagttactt catctttaat aacagaacgt acttaggaat tttatgagca   180
ttgttagtta gcatgacaca tgctatatgt attcgtcatt atgaataatg taaccacagc   240
aattacattg tacttttat tataaaaggg gggagggaa ggccctggtc cttttttaac    300
ttctgagagg tttcgattac taagtaagac cttatgtaga cttccatttg ggagctgaga   360
aagcagagga ttccaaaagg ggatgacatt tgcaaaggtc tagaaaagc gcctgggaat    420 tctaccgggt aggggaggcg cttttcccaa ggcagtctgg agcatgcgct ttagcagccc    480
cgctggcact tggcgctaca caagtggcct ctggcctcgc acacattcca catccaccgg    540
taggcgccaa ccggctccgt tctttggtgg ccccttcgcg ccaccttcta ctcctcccct    600
agtcaggaag ttcccccccg ccccgcagct cgcgtcgtgc aggacgtgac aaatggaagt   660
agcacgtctc actagtctcg tgcagatgga cagcaccgct gagcaatgga agcgggtagg    720 cctttgggc agcggccaat agcagctttg ctccttcgct ttctgggctc agaggctggg    780 aagggtggg tccgggggcg ggctcagggg cgggctcagg ggcggggcgg gcgcccgaag     840
```

```
gtcctccgga ggcccggcat tctcgcacgc ttcaaaagcg cacgtctgcc gcgctgttct      900
cctcttcctc atctccgggc ctttcgacct cacggtgttg ccaaaatgtc gctttccaac      960
aagctgactt tggacaagct ggacgtgaag gggaagcggg tcgtgatgag gtaattccgt     1020
actgctgccc tcaagccctc ggggccacat tctctctggc gtggcaagca cggttttccc     1080
atcaccttaa gttgcactta tttttcagct                                      1110

<210> SEQ ID NO 5
<211> LENGTH: 3157
<212> TYPE: DNA
<213> ORGANISM: Murinae gen. sp.

<400> SEQUENCE: 5
aagctttgtg atattaatgg cagactgctc tccaggtcca actgtttgac ttttaatt       60 ttttaaattt gcgctctgct gagggactca ggccttggtg tatgcaagac aagtgtccct    120
gtcctggcca cactcctagg cctgttgttt gttataaaag agatcacaag ggatacagac    180
caagcgaaaa taggggggg ctgtgagctt cattccctct cacatgatcc ctgcatatcc     240
agcaccctgc aaccagcttg ttcaaatctt gctcaagact gtaatagacc ttaatctgca    300
gtgaacacat ccttccgggg agatgggtga gcagggttga aagtcacagt tcttcccatc    360
actaaggaaa tcaaacagtt gcaaactcca tttcacatcc tatcagtggt ggagtacctt    420
aagattcaca tacggttgat cgggagctgg gagaggaaca ggaactggcc tcacagctta    480
atgagacctc tagaaagacg tttaaaggca gagggggtgt gtgaaaacaa gcaagggccc    540
tgatactcct tggtaaggct aaacacaaat gcctgcggga tggcatggga gagggcagat    600
atggatgtaa gctggcaagc catcagaagc tgagccgcac ccccctcccc ccatggtttg    660
ggagatggaa gtggggcagg agaaaggccc atctgatagg ctgctatggc ggatagaccg    720
gcacggtgct ggcatgtgct ttcacacaat atttactgaa ggcctgttgc ttgccaggag    780
ttgttcccgg cgccggaaca gcaatgaaga aagtgaccag gttttttctt gagtctcaca    840
agttttccgg tgaaggaggc ggaggatcga tgcatttcgg gctcctgctt ctgaggctga    900
ggagcatgtc gggttggcct ttctttgggg tgtcgcagca cacgtggagc cactcttgca    960
gggacatcgt gctgcgcgcg ccgccccggt ctcgtggcc tagccggctg gacgccgccc    1020
ccggcccagc ctacacgtgg gttcccgcac gtccgctggg ctcccactct gacgtcagcg    1080
cggagcttcc atttaaggcc ccgccgcgtg ctgctctgcg tgctggagcc actgtcgccg    1140
agctcggcca cgctgcttct cctcgccagt cgccccccca tcgtgcatct agcggtacgg    1200
ttgggcccca cgctgccggc acaggggtc ctatccgggg tggaggtgca gggtgttcag    1260
atttgggcac gcgtgggcta ctgtgctttg gggaacgtag caggcggccc acccagcctg    1320
ggcggcgaca cccgtgtaaa gaggactaag ggtggctggc ctgaaggttg ggagccaccg    1380 aacggggggcg agggagcggt gcgaaacttg agctcccgta actcgagcca tgggggccga    1440
aaaagccttg gcacgtccgg ggcggggtgct tcggagcagc cgtgcggttt gcatttttcct   1500 ttgcgtgggc tcggtggagt ggttgttttct gcagattata gggcgctctt gccctaaacg   1560
cattttgtta agaggctcgc tcctggtgtg actggggatc gtgctaaggc gctgcgtgcg   1620
gagaggaagc gggaagagtc gcagtccttc ctctgcaccc tagacggaag gaggaaacct   1680
gtagctgaga ggcctgcgac acccatcggt cgtaggtggg aagtagaggc accctgtcct   1740
aatagagcac agacttgagg tttgcgtgaa gtagattctc tgagggaaga agtccccacg   1800
ccctgccccc agtcagcaga gacctcacaa ggctgtctag aaatagcagc ggttgtaagg   1860
```

```
agaccggatt cctgcttgat ggccctagcg tgcttgccca gagatcttgt ccagtcctttt    1920 tgcactttgg aacgatttca aaaatagaca tggtgcttgc tgggaaaggt ggccatcgcg    1980
ggggtgggag tgggctccag gctcaggcct ccgcatattg tatccccatt ttggaactga    2040
agaaatttcc cttagcggcc acatcctggg taatgaggcc ccgcctggtg gtgaaggccc    2100
taatcctgtt agtggcattt tgagatctca ctctggcacc aggctaaggt ggctgccagc    2160
tccacttcac cgcgcttgtg ctttgggctc tagtaagggc caaactttga cgccgaactg    2220
cctgccagag gtctcatcca tggccagcag tcgctagacc tatatatatg cacctgattc    2280
tgaaattacg cgcactgcct tcccccgcct gccagtcttc tggatctggg ctggtcatac    2340
aacttgggtt cttgcgggg tgggggggtt agaagaagct tgcgcgtgca ggcttaagca    2400
cgttgctatg ccttggggtc gcaccttgtg gccgttattg gcgccctctg ctcttgattt    2460
ttggtacttc ctggagcaac ttggcgctct acttgctgta gggctctggg tgatgggaga    2520
agagcgggag ggcagctttc taaccatata agaggagata ccatcccctt ttggttcatc    2580
aagatgagta agtcctcagg cggctacacg tacacggaga cctcggtatt attttttccat   2640 ttcaaggtag agccttcctg gtagagccag aaccacatcc tgccgctgct attcttggtt    2700
ttccacttct gttctttgtc acattgtcac ttaatggaaa ggagtccaag gtagcaagtc    2760
agcgtttttt tttttttttt ttaaatacag ggacttggtg agtatacctt gggcaggtta    2820
caatgacaca cggtgtatac cccttaggtc tcaaaagatt caaagtccaa gatggcaacc    2880
ctcaaggacc agctgattgt gaatcttctt aaggaagagc aggctcccca gaacaagatt    2940
acagttgttg gggttggtgc tgttggcatg gcttgtgcca tcagtatctt aatgaaggta    3000
agtggagatc ttcatggccc aagctatggg tgtggtgtgg gggagaggac atccctacat    3060
tgtcacattg tatgtaaaac tatcaaggtt tgcacacact cagtcatctg tgaaacattt    3120
tgcaacataa tgatacacaa gaaagggatt atccaaa                            3157
```